US009976988B2

(12) United States Patent
Kollgaard et al.

(10) Patent No.: US 9,976,988 B2
(45) Date of Patent: May 22, 2018

(54) APPARATUS AND METHOD FOR INSPECTING A LAMINATED STRUCTURE

(71) Applicant: The Boeing Company, Chicago, IL (US)

(72) Inventors: Jeffrey R. Kollgaard, Seattle, WA (US); William J. Tapia, Graham, WA (US)

(73) Assignee: The Boeing Company, Chicago, IL (US)

(*) Notice: Subject to any disclaimer, the term of this patent is extended or adjusted under 35 U.S.C. 154(b) by 734 days.

(21) Appl. No.: 14/536,208

(22) Filed: Nov. 7, 2014

(65) Prior Publication Data

US 2015/0114124 A1 Apr. 30, 2015

Related U.S. Application Data

(62) Division of application No. 12/849,972, filed on Aug. 4, 2010, now Pat. No. 8,914,244.

(51) Int. Cl.
*G01N 29/04* (2006.01)
*G01B 5/28* (2006.01)
*G01N 29/07* (2006.01)

(52) U.S. Cl.
CPC .......... *G01N 29/04* (2013.01); *G01N 29/043* (2013.01); *G01N 29/07* (2013.01);
(Continued)

(58) Field of Classification Search
CPC ..... G01N 2291/044; G01N 2291/0422; G01N 29/043; G01N 29/07; G01N 2291/106
(Continued)

(56) References Cited

U.S. PATENT DOCUMENTS 3,863,826 A * 2/1975 Shoh .................. B29C 66/80
156/580
4,413,517 A 11/1983 Soden
(Continued)

FOREIGN PATENT DOCUMENTS

CN 201177617 Y 3/2008
GB 1171377 A 11/1969
(Continued)

OTHER PUBLICATIONS

UK IPO Search Report for GB1112980.6 dated Nov. 2, 2011.
(Continued)

*Primary Examiner* — Roy Y Yi
*Assistant Examiner* — Jeffrey Aiello
(74) *Attorney, Agent, or Firm* — Duft Bornsen & Fettig LLP

(57) ABSTRACT

Disclosed is an apparatus, method and system for inspecting structures, and more particularly for evaluating the condition of a structure. The disclosed nondestructive inspection testing method and apparatus enables an operator to assess the condition of a structure, such as a composite laminate part and determining the location and depth of anomalies. The method includes generating a subsurface longitudinal ultrasonic wave signal at a high incidence angle into a structure being evaluated and collecting at least one of any front, back or side reflected wave data. The method may include processing the reflected wave data to determine the condition of the structure, including any anomalies that may have been detected and their location, size and shape.

19 Claims, 11 Drawing Sheets

(52) U.S. Cl.
CPC ............... *G01N 2291/0231* (2013.01); *G01N 2291/0235* (2013.01); *G01N 2291/044* (2013.01)

(58) Field of Classification Search
USPC ......... 73/623, 627; 156/64, 378; 702/39, 42, 702/56
See application file for complete search history.

(56) References Cited

U.S. PATENT DOCUMENTS

| | | | |
|---|---|---|---|
| 4,510,812 | A | 4/1985 | Feng |
| 5,094,108 | A | 3/1992 | Kim |
| 5,596,989 | A | 1/1997 | Morita |
| 6,386,036 | B1 | 5/2002 | Borza |
| 7,222,514 | B2 | 5/2007 | Kollgaard et al. |
| 2005/0033177 | A1* | 2/2005 | Rogers ................... A61B 8/06 600/455 |
| 2005/0199065 | A1 | 9/2005 | Dunegan |
| 2006/0265175 | A1 | 11/2006 | Shimohamadi |
| 2007/0051177 | A1 | 3/2007 | Kollgaard |
| 2007/0239009 | A1* | 10/2007 | Kawashima ............ A61B 8/12 600/437 |
| 2008/0283332 | A1 | 11/2008 | Ihn |
| 2009/0066192 | A1* | 3/2009 | Taki ............... A61B 17/320068 310/354 |
| 2009/0192388 | A1* | 7/2009 | Yamada ............. B22D 17/2038 600/459 |
| 2010/0011865 | A1* | 1/2010 | Saxena ................. G01N 29/11 73/632 |
| 2010/0150726 | A1* | 6/2010 | Rose .................... F01D 5/3007 416/220 R |
| 2011/0166455 | A1* | 7/2011 | Cully ...................... A61B 8/12 600/463 |
| 2011/0197662 | A1* | 8/2011 | McAlister ............. G01N 1/405 73/61.59 |
| 2013/0039147 | A1* | 2/2013 | Witte .................. A61B 5/0093 367/7 |
| 2017/0042505 | A1* | 2/2017 | Havel ...................... A61B 8/12 |

FOREIGN PATENT DOCUMENTS

| | | |
|---|---|---|
| JP | 57158550 A | 3/1981 |
| WO | 2008157427 A1 | 12/2008 |
| WO | 2009/152143 A1 | 12/2009 |

OTHER PUBLICATIONS

NDT Resource center website, http://www.ndt-ed.org/educationresources/communitycollege/ultrasonics/cc_ut_index.htm, Apr. 14, 2010. Section on Angle Beam I.

Langenberg, K.J., et al., "On the Nature of the So-Called Subsurface Longitudinal Wave and/or the Surface Longitudinal "Creeping" Wave," Res Nondestr Eval (1990) 2:59-81, Springer-Verlag, New York.

Pilarski, A., et al., "Utility of Subsurface Longitudinal Waves in Composite Material Characterization," Ultrasonics, vol. 27, Jul. 1989, pp. 226-233.

* cited by examiner

APPARATUS AND METHOD FOR INSPECTING A LAMINATED STRUCTURE

RELATED APPLICATIONS

The patent application is a divisional of co-pending United States non-provisional patent application Ser. No. 12/849,972, filed on Aug. 4, 2010, which is hereby incorporated by reference.

TECHNICAL FIELD

The present disclosure relates generally to the inspection of structures such as composite fiber reinforced plastic (CFRP) used in aircraft or other structures, and more particularly to methods, apparatuses and systems for assessing the condition of a laminated structure.

BACKGROUND

Lightweight composite materials are being used more extensively in the aerospace industry for both commercial and military aircraft and other aerospace vehicles, as well as in other industries. The structures using these composite materials may be formed using multiple plies or layers of material that may be laminated together to form a high strength structure. These structures may undergo further machining processes during manufacturing and assembly of vehicles (drilling, cutting, countersinking, shimming, fastener removal, etc.); as well as further processes related to flight and ground operations (maintenance, repair, retrofit, or overhaul); and damages from an impact or other causes. The ability to characterize the condition of a laminated structure prior to delivery, repair, refurbishment, return to service, salvage, etc. may be required.

It would be advantageous to have a tool that can scan inside holes or cut outs in the structure to assess the condition of the composite in the vicinity of the drilled hole or machined edge, especially if a first delamination was identified with conventional longitudinal (L-wave) pulse echo ultrasound. Conventional pulse echo ultrasound is often reflected by the first delamination, and as a result it limits the operator from acquiring data on the delamination lying beneath it in a stratum of plies. Another difficulty is that conventional transducers with sufficient energy and appropriately narrow beam spread, are physically too large to be incorporated in a transducer wedge that can be inserted in a small hole for inspection of the structure open to the hole.

A further disadvantage of existing solutions is that the maximum depth of the damage is unknown without repeated cycles of inspecting and sanding which results in removal of overlying material. Since repairs often require a 30:1 taper on the sanded-out crater or "scarf"; small damage that is only a few plies deep can result in a large repair surface area that intrudes on other structures, and requires major disassembly. Large repairs also may result in a large area exposed to heat when the repair plies are cured. Further, the time spent in repeated cycles of inspection and sanding to establish the eventual repair size can be considerable. Often, intermediate inspections reveal damage that was not discernible prior to the start of damage removal operations. As a result, the repair scope changes mid-way through the process and engineering must reconsider the overall size of the repair and its impact on surrounding structure.

In addition, there is a need for "one shot" inspection methods to assess the condition of a structure. For example, having a tool to locate and map damage or delamination in plate-like structures, down through multiple plies open to the drilled holes or machined cut-outs, would allow an operator to quickly inspect the structure around the drilled hole. Current methods do not allow inspectors to characterize the condition in "one shot process", and thereby hampers early development of a plan that encompasses the magnitude of the subsequent repair.

Visual and remote visual inspection methods are also used to try to image delamination in damaged areas and drilled holes, but experience has shown that some delamination are missed by visual inspection, while being detected by ultrasonics. This may be due to tightness of the delamination, glare conditions in the hole, or drilling dust filling the delamination surface.

It would therefore be desirable to provide improved techniques for inspecting a structure. The foregoing examples of related art and limitations associated therewith are intended to be illustrative and not exclusive. Other limitations of the related art will become apparent to those of skill in the art upon a reading of the specification and a study of the drawings.

BRIEF SUMMARY

It is an object of the present disclosure to eliminate or reduce the above described disadvantages. The following embodiments and aspects thereof are described and illustrated in conjunction with an apparatus, method and system to be exemplary and illustrative, not limiting in scope.

In accordance with an embodiment, an apparatus is disclosed for generating ultrasonic longitudinal waves into a structure, for example to inspect the area open to a machined hole, cut-out, or edge in composite laminates. The ultrasonic transducer assembly comprises a transducer, a mechanical coupling mechanism, and a transducer rod having a first and second end of the propagation axis of the rod. The first end is coupled to the transducer utilizing the mechanical coupling, and the second end is a flat face orientated non-normal to the propagation axis of the rod. Variations on the ultrasonic transducer assembly are provided, wherein the transducer rod second end may have a variety of configurations including: a curved face, a conical face, or is multifaceted. Further, single or multiple transducer crystals may be embedded in the transducer rod itself, to provide direct incidence on the structure without use of the reflecting transducer element, or in combination with it.

In accordance with another embodiment of the disclosure, a method of inspecting a structure is disclosed and may include generating and reflecting an ultrasonic longitudinal wave (LW) within a transducer rod, prior to launching the wave into a structure being evaluated, and collecting at least one of any echo wave data to assess the condition of the structure. The method may also include generating a subsurface longitudinal wave (SSL) in the structure for the purpose of interrogating the structure. Further the method may be used to inspect a structure for anomalies, and may include processing at least one echo wave to measure a size, location, and shape of an anomaly. The method may further include inspecting a machined hole or edge in a composite laminate for anomalies such as a delamination. Another variation on this method would be to scan, move incrementally, or translate the ultrasonic transducer assembly to orient the transducer ultrasonic exit point relative to the structure. A further variation is to convert the echo wave electrical signal to acquired data, then store it, and later retrieve the stored data for analysis. The analyzed data may be used to determine the condition of the structure based on at least one echo wave associated with the subsurface longitudinal wave in the structure. A further variation on this embodiment may be the mapping of the anomalies in a particular structure.

In accordance with another embodiment of this disclosure, a system for inspecting a structure is described; the system comprising at least one ultrasonic transducer assembly with at least one of the transducers configured to transmit and receive ultrasonic energy, at least one reflective rod element, at least one ultrasonic pulser/receiver operatively coupled to the at least one ultrasonic transducer; a computing system operatively coupled to the ultrasonic pulser/receiver, the computing system, further comprising a data acquisition component, a data analysis component, and a display component. A variation on the embodiment includes a pulse echo longitudinal ultrasonic transducer. A further variation on the system is a translating mechanism operatively coupled to the ultrasonic transducer assembly and the computing system, or alternatively the system may include a type of holder or spring that holds the ultrasonic transducer assembly in a particular position. An additional variation is a storage medium configured to store the acquired data. Further the data acquisition system is capable of characterizing the condition of the structure based on at least one echo wave associated with the pulsed subsurface longitudinal sound wave.

In accordance with another embodiment, disclosed is a method for inspecting an airplane utilizing the pulse echo longitudinal wave ultrasonic wave nondestructive inspection (NDI) methods and apparatus as disclosed herein to determine whether the part condition exceeds allowables, and ensures that non-conformances are documented in accordance with specifications. A variation on this airplane test method would be to scan, move incrementally, or translate the ultrasonic transducer assembly across the airplane to orient the transducer ultrasonic exit point relative to the airplane. A further variation is to convert the echo wave electrical signal to acquired data, then retrieve the stored data for analysis. The analyzed data may be used to determine the condition of the airplane based on at least one echo wave associated with the subsurface longitudinal wave in the structure.

DETAILED DESCRIPTION

The following detailed description refers to the accompanying drawings, which illustrate specific embodiments of the disclosure. Other embodiments having different structures and operations do not depart from the scope of the present invention.

Figure 1:
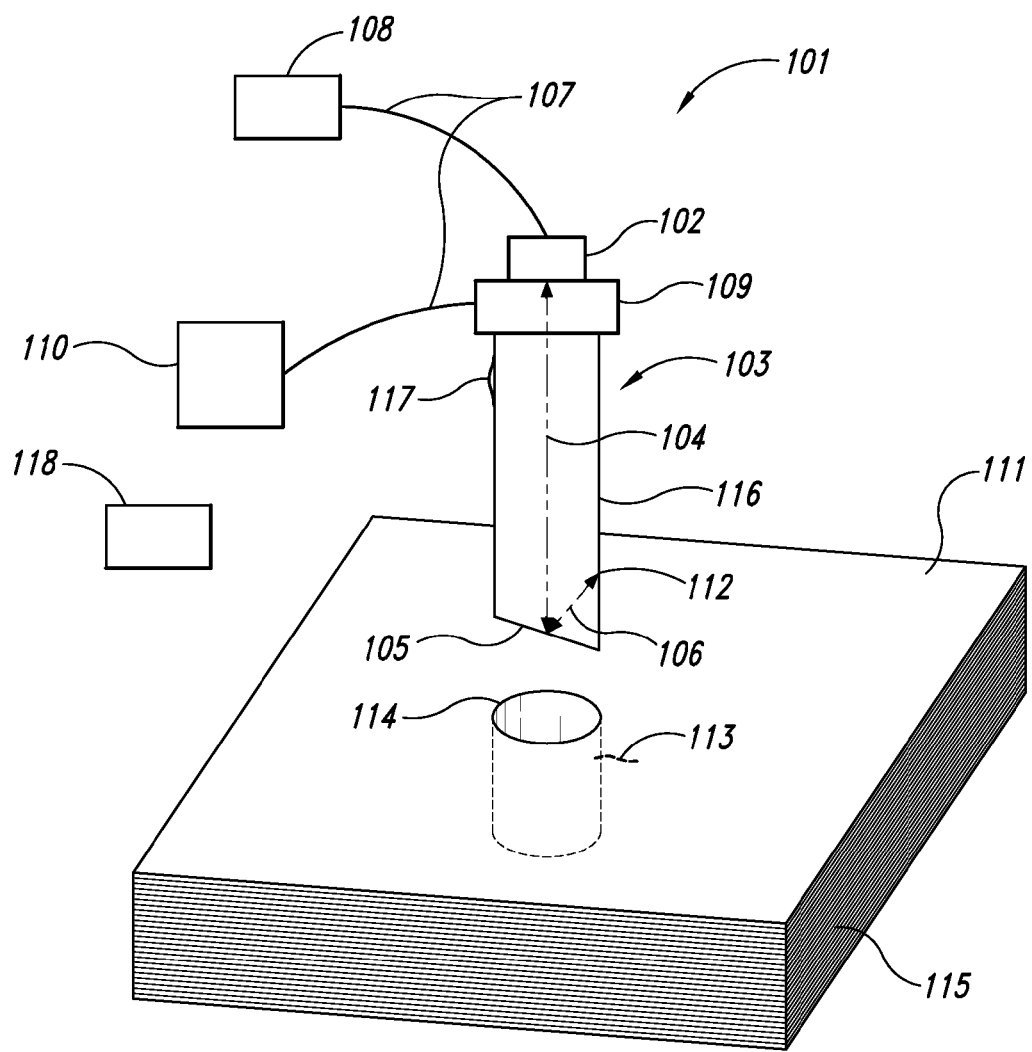
FIG. 1 is an illustration of an apparatus embodiment disclosed. The ultrasonic transducer assembly utilizes at least one flat, angled reflective rod element. The single transducer is used in pulse-echo mode, and both transmits a pulse and measures the reflected or echo signal.

FIG. 1 is an illustration of an apparatus embodiment. The ultrasonic transducer assembly 101 utilizes a novel reflective rod element 105. The reflective rod element can be any number of alternate geometries including but not limited to a single flat face, or multiple facetted angles, curved face, or conical geometry. The ultrasonic longitudinal sound wave (also called an L-wave for short) 104 is produced at the piezoelectric transducer 102 and propagates down the transducer rod 103 to the reflective rod element 105, where it is reflected to the side 116 of the transducer rod 103. After reflecting off the reflective rod element 105, the reflected L-wave 106 is transmitted to the side 116 of the transducer rod 103, and may be focused with other reflected L-waves depending on geometry of the reflective rod element.

In this example, the transducer rod 103 is moved into the hole 114, and positioned proximate to the structure open to the hole, and the reflected L-wave will be launched from the transducer rod exit point 112 into the laminated structure 115, resulting in an ultrasonic subsurface longitudinal wave (SSL-wave) propagating through the structure. The condition of the drilled hole is to be inspected, including the detection of an anomaly 113 in the structure (such as a delamination within the plies). As the SSL propagates through the material, a reflected sound wave or 'echo wave' is transmitted back to a receiver in the piezoelectric transducer 102 via the original route it was launched, i.e. via the transducer rod 103, and the reflecting rod element 105. Those skilled in the art of pulse echo ultrasonic inspection are aware that certain transducers can both transmit and receive ultrasonic signals. The echo sound wave associated with an anomaly, can be differentiated from the echo sound waves in the nominal regions of the structure with signal processing. In this illustration the transducer is coupled to the rod via a mechanical coupling 109. A translating mechanism 110 can be used to move the apparatus in multiple directions, including either vertically, horizontally and circumferentially inside the exemplary hole or cut-out or across the surface of the part 111. The ultrasonic transducer assembly is interfaced with the ultrasonic test instrumentation 108, which includes the power supply, pulser/receiver, computer interface, hardware and software, instrument control, and signal processing via wires or cables 107 or controlled wirelessly. Optional accessories may include any number of items including, but not limited to a leaf spring 117, a rod holder 118 or hole adaptor, that may be used to keep the transducer proximate to the material. An optional thumbwheel collar can be used for axial indexing.

The reflective rod element 105 on the second end of the transducer rod 103 alters the pathway of the sound wave through the transducer rod; changing the wave path from the propagation direction of the transducer, and reflecting it to an exit point 112 on the side 116 of the transducer rod 103, for a more effective launch of the ultrasonic signal into the proximate structure 115 under inspection. The disclosed transducer configuration is especially helpful because the rod design enables the introduction of ultrasonic sound wave entry down into small holes in the structure under test, that would not otherwise accommodate transducers of conventional size, allowing the inspector to assess the condition of the structure opened by the hole and determine size, position, and shape of any anomaly if they exist, and to map the distribution of the anomalies with the additional signal processing in the ultrasonic instrumentation 108. It is also an object of the apparatus to provide sufficient depth resolution to have the ability to separate flaws that are close together, and to have sufficient sensitivity to detect anomalies of a specified minimum size. The apparatus can be used on a variety of portholes in composite structure for non-destructive inspection including but not limited to drilled holes, edges, pass-throughs, slots, cuts, access panels or wing leading edges.

Figure 2:
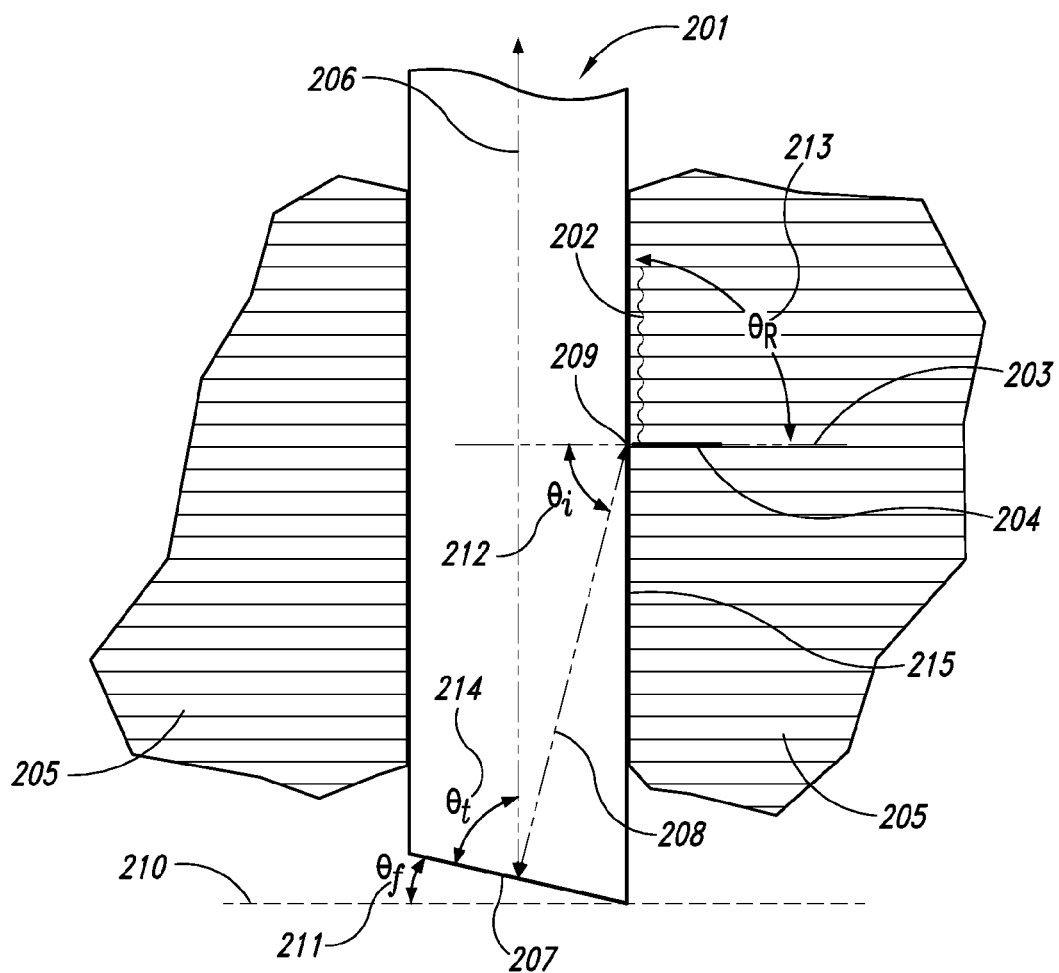
FIG. 2 illustrates a single longitudinal wave launched from the ultrasonic transducer assembly into the structure, and interacting with an anomaly such as a delamination in a composite laminate structure.

FIG. 2 is a side view of the transducer rod positioned in a composite laminate hole and depicts the interaction of the sound wave with a delamination in the laminate. An ultrasonic longitudinal sound wave (also called an L-wave) 206 propagates down the transducer rod 201 and then is reflected off the reflective rod element 207. Upon reaching the exit point 209 of the transducer rod, the reflected sound wave 208 is launched into the laminated structure 205 at a high incidence angle relative to the perpendicular 203 of the measuring surface 215, and produces an ultrasonic subsurface longitudinal wave (also known as a SSL-wave) 202 in the material propagating through the structure. As the SSL wave propagates through the material it can encounter both nominal and anomalous areas. By processing the return signal from the echo wave, an anomaly 204 in the structure, can be detected and differentiated from nominal areas.

Depending on the material composition of both the structure and the transducer rod, and the velocity of the sound wave in each material type, an optimum entry angle can be determined. Tests revealed that incident angles in the range of 50 degrees to 70 degrees launched from a polystyrene transducer rod (Rexolite®) into composite fiber reinforced plastic (CFRP) produce waves that propagate over the longest distances. Steeper angles also produce waves, but they do not propagate as long beneath the rod exit point, rather they peak at higher amplitudes. Additional calculations suggest that 54 degrees would be the optimum angle for generation of the SSL wave in carbon reinforced plastic (CFRP) as shown in the following paragraphs.

The ultrasonic subsurface longitudinal wave generated by the apparatus is robust across different structures, and is tolerant of a range of incident angles. By using the calculated material velocity, one can calculate the angle needed to induce a near 90 degree wave into the structure. The ultrasonic subsurface longitudinal wave velocity has been measured in a number of materials including CFRP. In this example, the velocity in CFRP is on the order of 0.114 in/usec (2900 meters/sec), and the velocity in Rexolite® is 0.092 in/usec (or 2333 meters/sec). The incident angle of the wave is calculated as:

$$\frac{\sin\theta_i}{V_1} = \frac{\sin\theta_R}{V_2}$$

Sin $\theta_i$=Angle of incidence that is needed onto the structure, at the exit point of ultrasonic transducer rod
Sin $\theta_R$=Angle of refraction relative to the normal into the structure (~90 degrees)
$V_1$=Ultrasonic velocity in transducer rod material (e.g. Rexolite®)
$V_2$=ultrasonic velocity in test material (e.g. CFRP)

$$\frac{\sin\theta}{.092 \ in/usec} = \frac{\sin 90}{.114 \ in/usec}$$

$\sin\theta = 53.8$ degrees

FIG. 2 illustrates the angle of incidence $\theta_I$(212) to be 53.8 degrees at the transducer rod exit point 209, and the angle of refraction $\theta_R$(213) into the structure near 90 degrees. The bevel angle on the reflective rod element was determined by subtracting the incident angle from 90 degrees, then dividing by two to account for the incident and reflective angle on the bevel edge as follows.

90−53.8=36.2 degrees;

36.2 degrees/2=18.1 degrees

In practice, the number is often rounded off to 18 degrees.

As described in the preceding, the reflective rod element (207) in this example was fabricated with a 18 degree bevel, and is indicated as $\theta_F$ (211) relative to the normal to the transducer axis (210). The angle enclosed by the flat reflective edge and the transducer axis, $\theta_T$ (214) is 54 degrees.

Figure 3A:
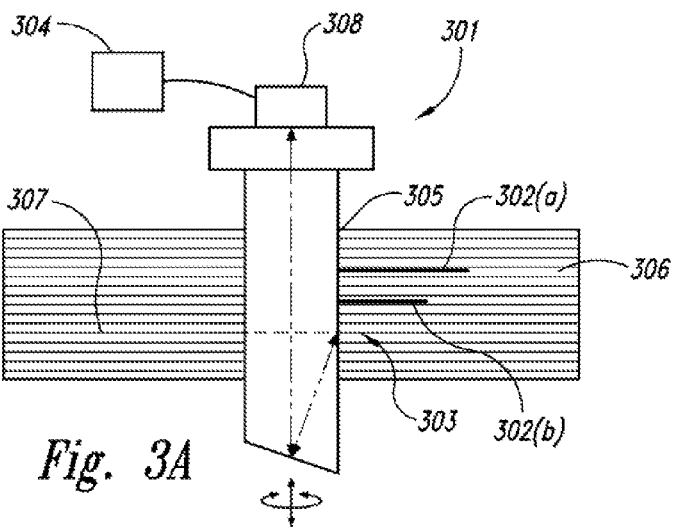
FIGS. 3A, 3B, and 3C illustrate an embodiment of the apparatus as it is moved incrementally to examine the structure made open by a drilled hole in a composite structure exhibiting multiple anomalies, such as a delamination, as well as nominal areas along the hole surface.
Figure 3B:
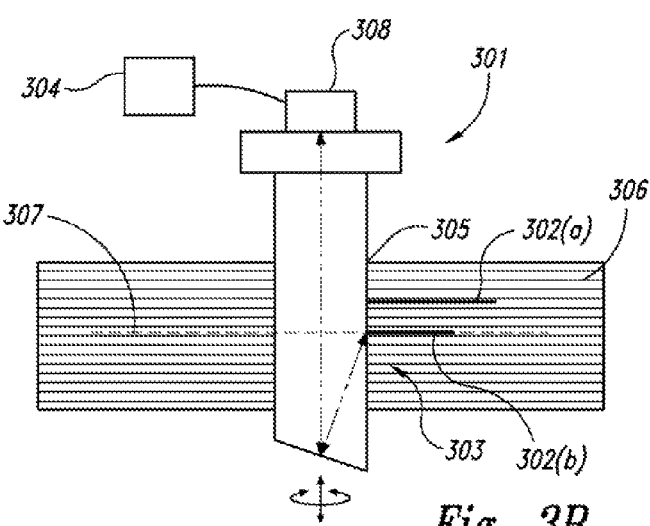
Figure 3C:
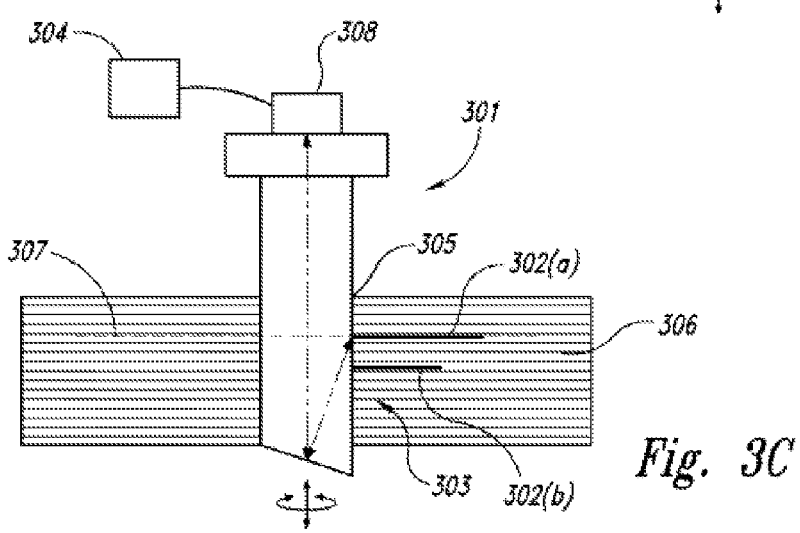

FIGS. 3 A-C are illustrations of a single ultrasonic transducer assembly 301 that has been moved up incrementally in a hole via a translating mechanism 304, and was used to examine the condition of the composite plies surrounding a drilled hole or cut-out in a composite laminate structure. FIG. 3A depicts a transducer rod 305 that is positioned at a depth of one of the composite laminate ply layers 307 and was determined to be of acceptable condition and containing no flaws 303. In contrast, FIG. 3B illustrates an area under interrogation that has a delamination 302(b). In FIG. 3C, the transducer has been moved up further still in the hole, and is positioned to interrogate an area with a second delamination 302(a) in the laminated structure 306. The ultrasonic transducer assembly 301 contains a transducer 308 that is configured for both transmitting and receiving ultrasonic sound waves. It captures the reflecting or echo wave from the non-flawed areas 303, or the area with an anomaly 302, and other depths for further processing. Operators can perform time-gating of the signals from a multitude of depths or plies 307 within the structure, or by orienting the transducer to the fibers in a specific layer or ply of interest. Alternatively, the transducer could have been lowered into the hole, and the order of inspection points may have been reversed, for instance first 302a, then 302b, and last 303.

The sound path through the ultrasonic transducer assembly 301 is essentially the same, whether the signal is launched at 302(a), 302 (b) or 303. This enables the operator to look at the portion immediately after the entry point into the structure, and set a narrow alarm gate there. As the probe is incremented into the hole, the sound path and alarm gate position remain unchanged and an anomaly at the sound exit point will trigger the gate (in this example that would be the delamination). Alternatively, the operator may set a wider gate on the propagating sound wave and increment fewer times and that might be sufficient for a particular structure. In some cases it might be useful to let the sound wave propagate all the way to the surface (from say, 0.25" deep) and look for things that interrupt the surface echo. This would enable identification of damage too small to create echo signals, such as distributed micro-cracks, heat damage or "delamination clouds". The process may be repeated to obtain a map of the anomalies and acceptable areas that have been detected across the area open to the porthole and scanned with the apparatus. Further, this configuration is all readily adaptable to C-scan using a narrow alarm gate, and an encoder for radial and axial position (e.g. rack and pinion for axial depth measurement and encoding), and for automating to move from hole to hole.

The illustration underscores the benefit provided by this apparatus to be able to scan inside holes to determine if any delamination exists, including those delamination beyond the surface delamination identified with conventional L-wave ultrasonics from the outside of the structure. In this particular illustration, the delamination identified as 302(b) would likely have been obscured by delamination 302(a) identified by conventional inspection methods and would have gone undetected without repeated scarfing and sanding without the embodiments disclosed here.

The term 'structure" is not meant to be limiting, as the disclosed apparatus could be used to inspect any number of parts or structures of different shapes and sizes, such as manufactured parts, machined parts or existing structures that are being inspected for a variety of purposes. Further, the structure to be inspected could be composed of any number of materials, though one of the main uses is for inspecting plate-like structures such as composites laminates including fiber-metal laminates or other carbon fiber reinforced plastic structures. Similar needs exist and similar benefits may be realized, over other materials in structures that require quick, frequent or infrequent inspections periodically over time to assess health of the structure. Further, the apparatus could be used to inspect any number of structures in a variety of industries where the condition of the structure is required or desired, such as in the aircraft, automotive or construction industries. The apparatus is not limited to inspecting holes alone, alternative embodiments include structural access cut-outs, pass-throughs, slots and access panels (e.g. as for a wing leading edges); generally any structure with a porthole or an edge. Though one example described herein is for detecting a delamination in a composite structure resulting from machining activity or damage effects; the apparatus is not limited in that regard either, and alternatively the apparatus may be used to monitor the condition of structures within acceptable levels over time for health maintenance activities.

The disclosed apparatus whether for hole or edge inspection, is generally capable of moving over a smooth, relatively rough, complex, and/or contoured surface while maintaining the desired orientation and proximity with the structure to transmit a sound wave towards or within the structure. Whether for inspecting portholes or edges, optional accessories for scanning, translating, and holding the ultrasonic transducer assembly proximate to the structure may be employed to assist in the inspection.

The disclosed ultrasonic transducer assembly may alternatively utilize multiple transducer crystals, including one that may be embedded in the transducer rod itself at various locations, to provide direct incidence on the structure in combination with the reflecting transducer element, or without it. Further, multiple transducer crystals may be embedded at regular axial locations to reduce or eliminate the need to index the probe in and out of the hole.

Figure 4:
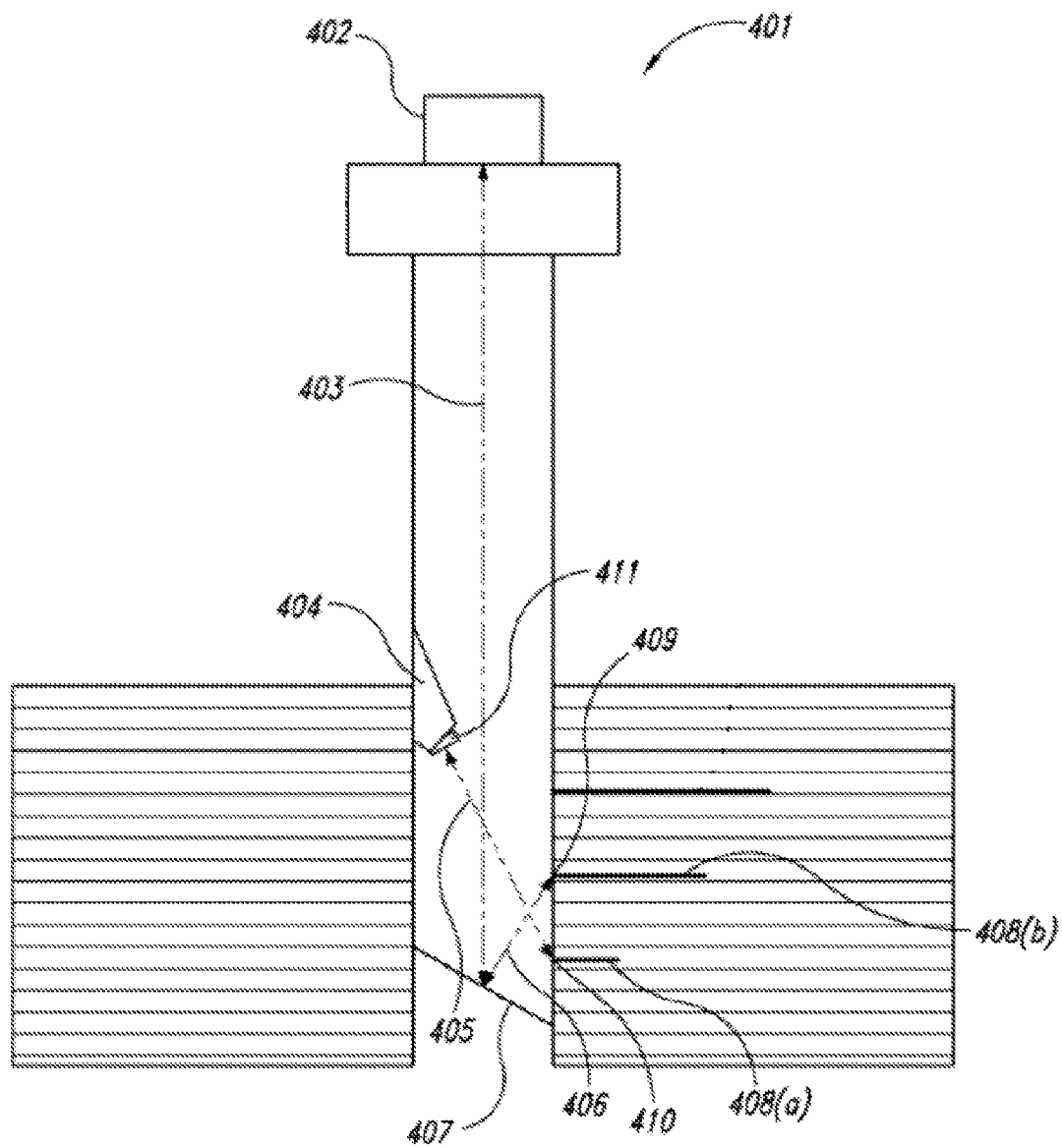
FIG. 4 illustrates a variation of the apparatus embodiment incorporating two transducers into one ultrasonic transducer assembly. One of the propagating sound waves reflects off the reflective rod element, while the other sound wave does not.

FIG. 4 illustrates an ultrasonic transducer assembly 401 with a first and a second piezoelectric transducer 402 and 404. One piezoelectric transducer 402 is shown at the top of the ultrasonic transducer assembly 401, and the second piezoelectric transducer 404 is embedded lower in the rod, and is focused by a lens 411. Piezoelectric transducer 402 produces the first ultrasonic sound beam 403 that reflects off the reflective rod element 407, resulting in a reflected sound beam 406 that propagates to the exit point 409 at the side of the transducer rod. The second sound beam 405 produced by the second piezoelectric element 404 propagates to the exit point 410 on the side of the rod impinging directly without a reflection off the reflective rod element. Utilizing two piezoelectric transducers in the ultrasonic transducer assembly enables the operator to launch two sound beams that can be propagated to different exit points on the transducer rod. In this illustration, the transducers are positioned to see two different ply depth areas inside the hole and will detect two anomalies, one above the other (408a and 408b). The launch of the two sound beams is not limited to a particular sequence, rather it may include, but not limited to, launching the sound beams simultaneously, periodically, synchronized, instantaneous, consecutive, concurrent, timed, or with increasing/decreasing frequency.

Although the disclosed ultrasonic transducer assembly shown in many of the previous figures depicts a single transducer capable of generating and receiving sound waves, the disclosed apparatus is not limited to that configuration. Rather, the receiving sensor may be separate from the transmitting transducer. In a related fashion, multiple transducer could be placed in a pitch-catch arrangement within the rod. Alternatively, two transducers having transmit/receive sensors may be configured to capture echo wave signals, allowing each transducer to measure the difference in transit time between the echoes received at each of the two transducers. This may be simpler to implement than a measurement of the transit time between an emitting transducer and a receiving transducer which entails knowledge of the instant at which the emitting transducer emits a wave. Further benefit may be reached by taking advantage of the fact that one of the transducers has a shorter sound path and the minimization of echoes in contrast, relative to the other transducer.

Figure 5:
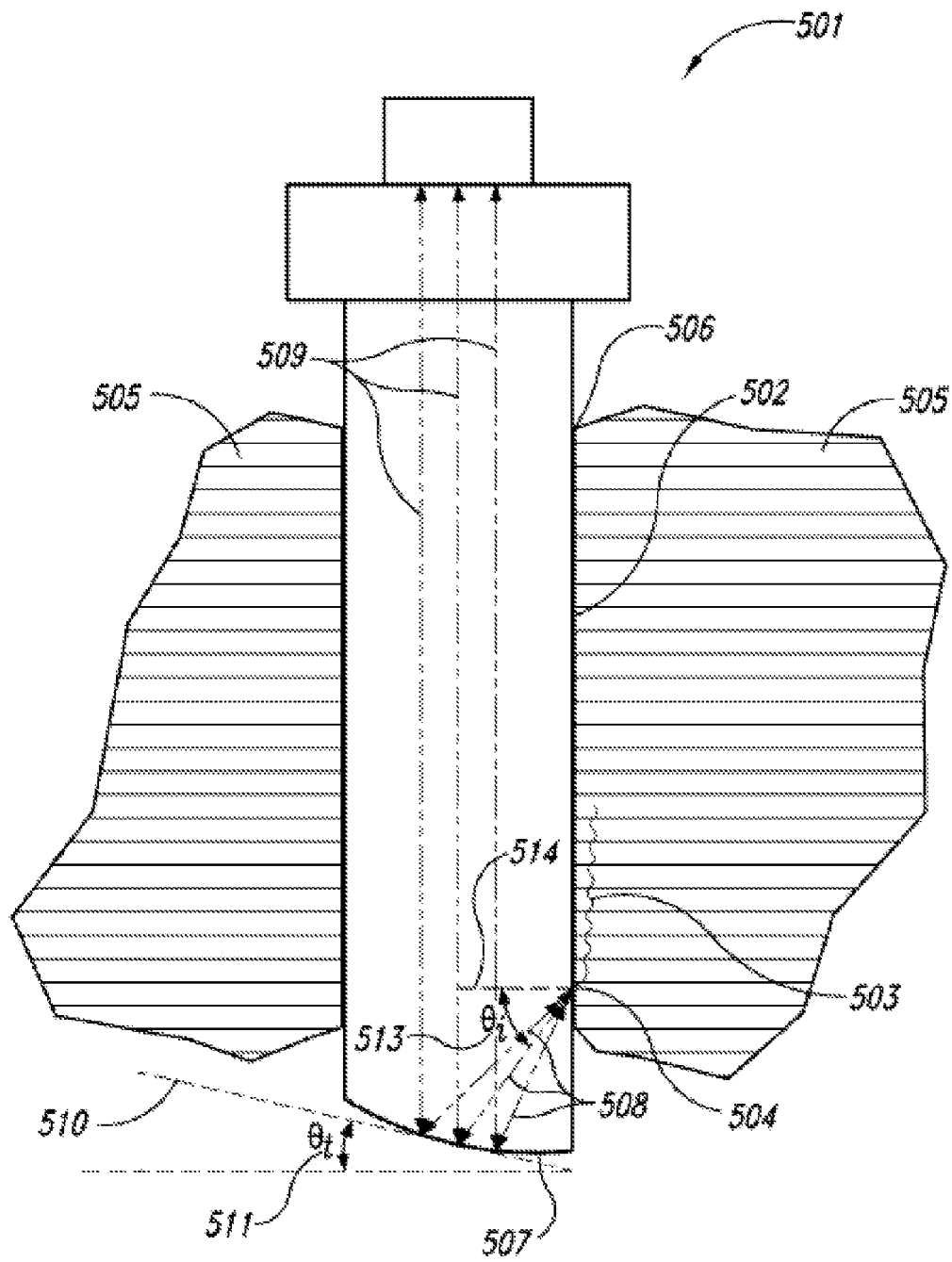
FIG. 5 illustrates another variation of the apparatus embodiment, and depicts a curved reflective rod element on the transducer, instead of a flat angled reflective rod element.

FIG. 5 illustrates an alternate embodiment of an ultrasonic transducer assembly 501 incorporating a curved reflective rod element 507 on the transducer rod. The ultrasonic transducer assembly is positioned within a hole 506 drilled into a composite laminate structure 505. The curved reflective element focuses and redirects the longitudinal sound wave 509 to the side 502 of the transducer rod where the reflected sound waves 508 can be launched into the laminated structure 505 from the exit point 504 at an optimized angle 513, and producing the subsurface longitudinal wave 503.

To determine the exit point location on the side of the transducer rod, calculations are performed based on finding the parabolic focus of a curved surface for the reflective rod element. By envisioning the center of transducer sound beam along the transducer rod axis and the toe of the rod situated at the mathematical origin (0,0), and knowing the entry angle of the sound wave into the structure and the rod diameter, a general equation can be built as follows:
Slope at a point on a parabola using x,y coordinates:

$$y=ax^2$$

The tangent of the parabola described by equation $y=ax^2$ has slope equal to:

$$\text{Slope}=dy/dx=2ax$$

Parabolic Focus:

$$\text{Slope}=\tan((90°-\theta)/2)$$

$$\text{Slope}=\tan(45°-\theta/2)$$

Therefore:

$$\tan(45°-\theta/2)=2a(d/2)$$

$$\tan(45°-\theta/2)=ad$$

$$a=\tan(45°-\theta/2)/d$$

where: d=diameter or the rod
a=the parabola constant
To find the focal point (F):

$$F=1/(4a)$$

Applying these equations to an actual situation, we can determine the parabolic focus for a 0.495" diameter rod made of Rexolite, with the center sound beam to be launched into the structure at angle θi of 53.5°:
Find the parabola constant:

$$a=\tan(45°-\theta/2)/d$$

$$a=\tan(45°-(53.5°/2))/0.495"$$

$$a=0.6662"$$

Find the focal point or exit point of the transducer rod:

$$F=1/(4a)$$

$$F=1/(4(0.6662"))$$

$$F=0.3753"$$

In FIG. 5, the angle of incidence $\theta_i$ into the structure is shown as 513. This angle is formed by the line 514 perpendicular to the axis of symmetry of the transducer rod and the pathway of the middle reflected sound beam 508. The line tangent 510 to the curved reflective rod element (507) is shown, and the bevel angle is indicated by $\theta_t$ (511) in this example. Angle $\theta_t$ (511) is enclosed by the tangent line 510 and a line perpendicular to the axis of the transducer situated at the mathematical origin 0,0.

Figure 6A:
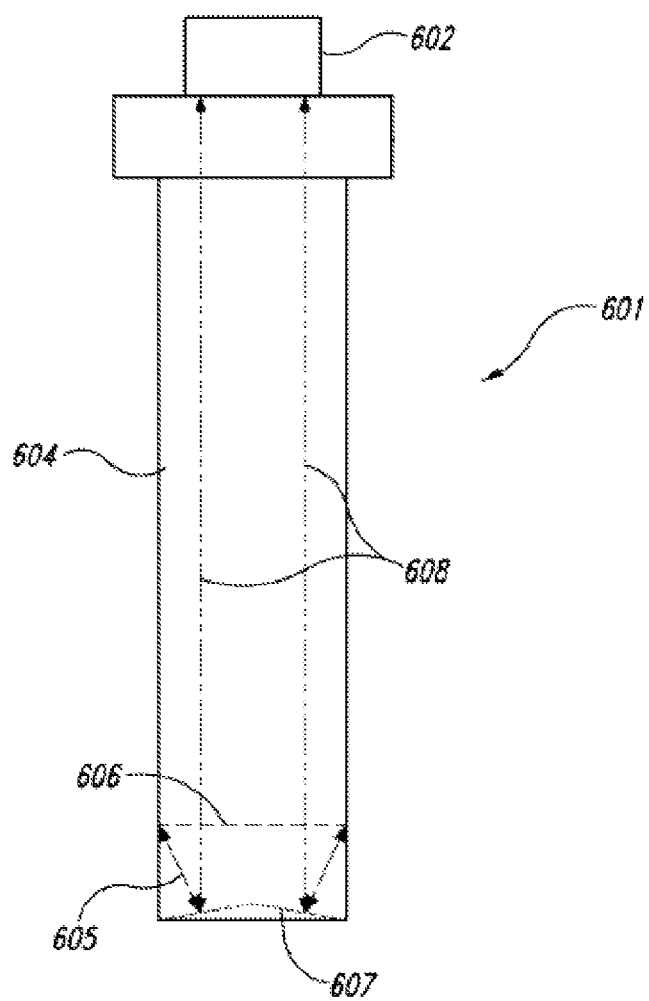
FIGS. 6A and 6B are an illustration of another variation of the apparatus embodiment, illustrating a transducer with a conical reflective rod element.
Figure 6B:
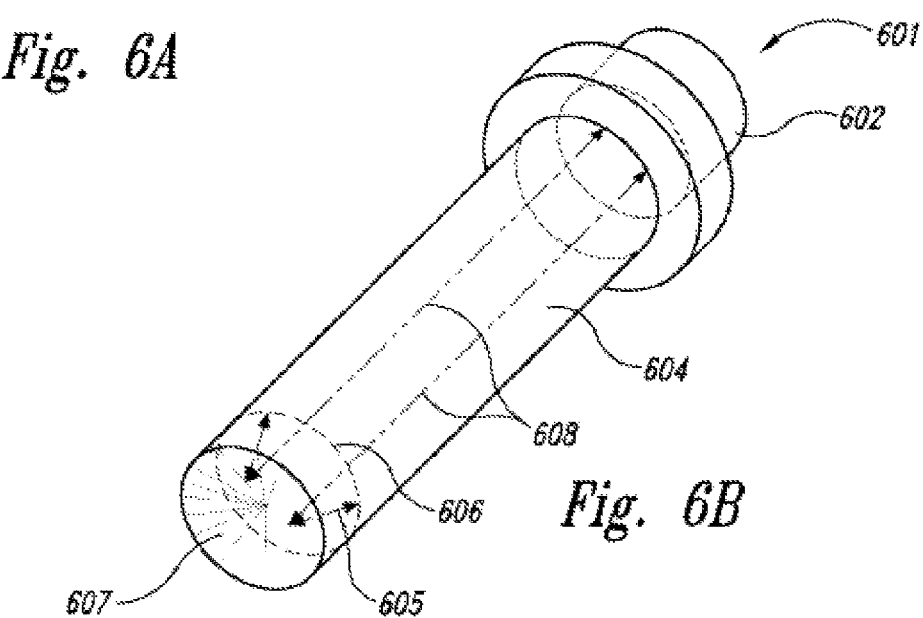

FIG. 6 illustrates an alternate embodiment of the ultrasonic transducer assembly 601. The reflective rod element 607 is cone-shaped, rather than curved or a flat bevel. A conic reflective rod element may be employed to eliminate the need to spin the probe in the hole for 360-degree scan coverage. Alternatively a faceted array of crystals could be embedded circumferentially.

With the transducer sound waves modeled as a collection of parallel rays, two such sound waves 608 are shown illustrating the sound path from the transducer 602 to the conic reflective element 607. Each reflected sound wave 605 is transmitted to the exit point 606 along the side of the transducer rod 604. With a multitude of sound rays, a ring of exit points 606 are formed around the side of the longitudinal transducer rod enabling the operator to launch a ring of sound waves into a structure, without the need to circumferentially rotate the transducer rod.

Figure 7:
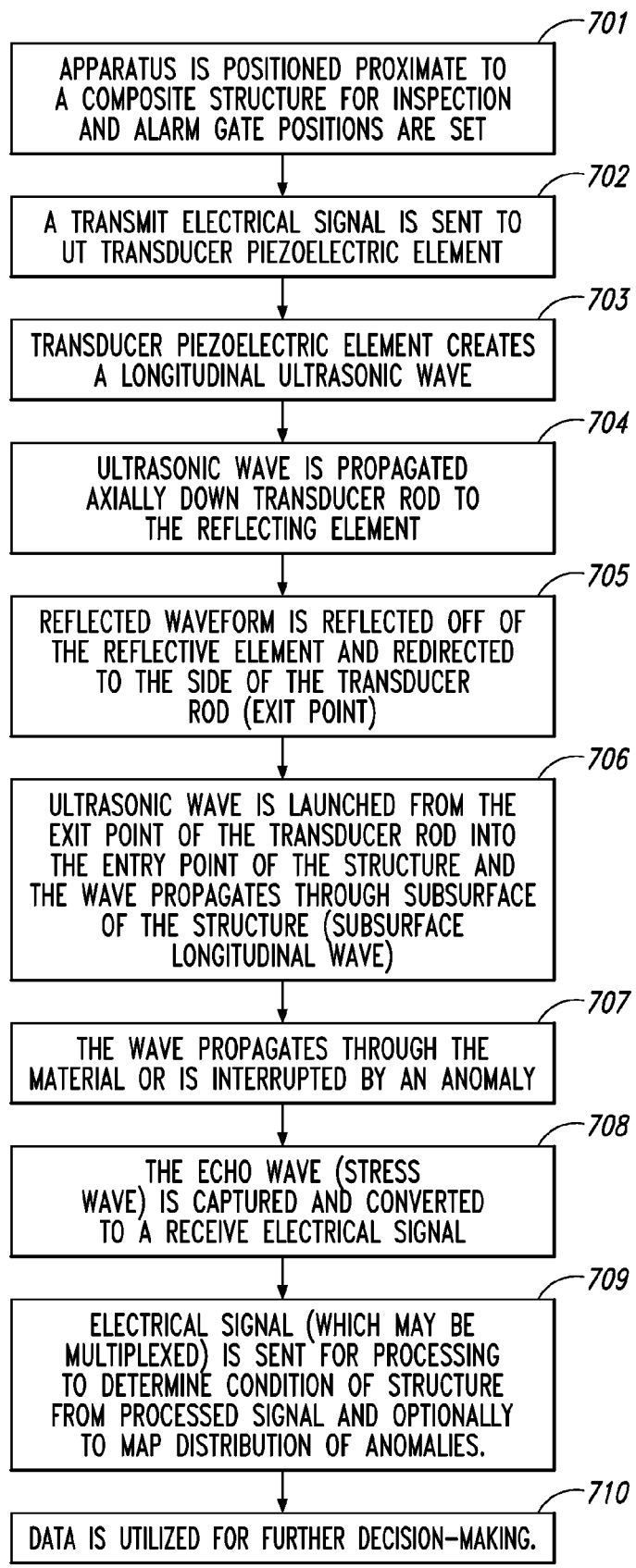
FIG. 7 is a flow chart illustrating one variation of a method for inspecting holes or a cut edge in a structure.

FIG. 7 is a flow chart illustrating the method for assessing the condition of a structure, such as a composite laminate. In block 701, the ultrasonic longitudinal wave transducer is positioned proximate to the composite structure. A transmit electrical signal, such as a spike or square wave is transmitted to the UT transducers 702. A longitudinal wave is generated by the transducer piezoelectric element 703. The ultrasonic wave is propagated axially down the transducer rod to the reflecting element 704. The wave is reflected off the reflective element and redirected to the side of the transducer rod at the exit point 705. The ultrasonic wave is launched from the exit point of the transducer rod into the entry point of the structure and the wave propagates just below the surface of the structure as a subsurface longitudinal wave 706. If the propagating sound wave is interrupted by an anomaly, the sound wave is reflected or scattered, otherwise the sound wave continues to propagate through the subsurface of the structure until it dissipates 707. The echo wave (stress wave) is captured and converted to a 'Receive' electrical signal 708. The electrical signal is sent for further processing 709 to provide an indication of the condition of the structure from processed data, and optionally can be used to map distribution of anomalies (such as a delamination). The information can be used for further decision making 710.

The disclosed nondestructive inspection testing method enables an operator to assess the condition of a structure, such as a composite laminate part, and determine the location and depth of anomalies. The method includes generating a subsurface longitudinal ultrasonic wave signal at a high incidence angle into a structure being evaluated and collecting at least one of any front, back or side reflected wave data. The method may include processing the reflected wave data to determine the condition of the structure, including any anomalies that may have been detected and their location, size and shape. Further, in accordance with this embodiment, the disclosed method can be used to determine if additional delamination exists beyond the surface delamination found by way of a conventional ultrasonic pulse echo L-wave inspection.

A further variation of this embodiment, is disclosed as a method for inspecting the free edge of a structure. By utilizing the ultrasonic transducer assembly along the edge of the structure, the condition of the structure can be determined. As an example, a machine cut edge or an access panel could be inspected by this method.

The third embodiment relates to a non-limiting, exemplary system for nondestructive inspection of a structure. At least one ultrasonic transducer assembly is proximate to the surface of the structure, and configured to transmit and receive ultrasonic energy to and from the structure. An ultrasonic pulser/receiver is operatively coupled to the at least one ultrasonic longitudinal transducer. A computing system is operatively coupled to the ultrasonic pulser/receiver. The computing system includes a data acquisition component configured to acquire data from the ultrasonic pulser/receiver and a data analysis component configured to analyze the acquired data. The data analysis component may be further configured to analyze the acquired data for the condition of the structure. The system may also be configured to include a translation and rotation mechanism and controller for incrementing the transducer in various directions and circumferentially in a hole; and also accessories for situating the rod holder, such as a leaf spring, rod holder or adapter, and a thumbwheel collar. During inspection, the data acquisition component coupled to the ultrasonic pulser/receiver displays the processed signals on the display screen.

Figure 8:
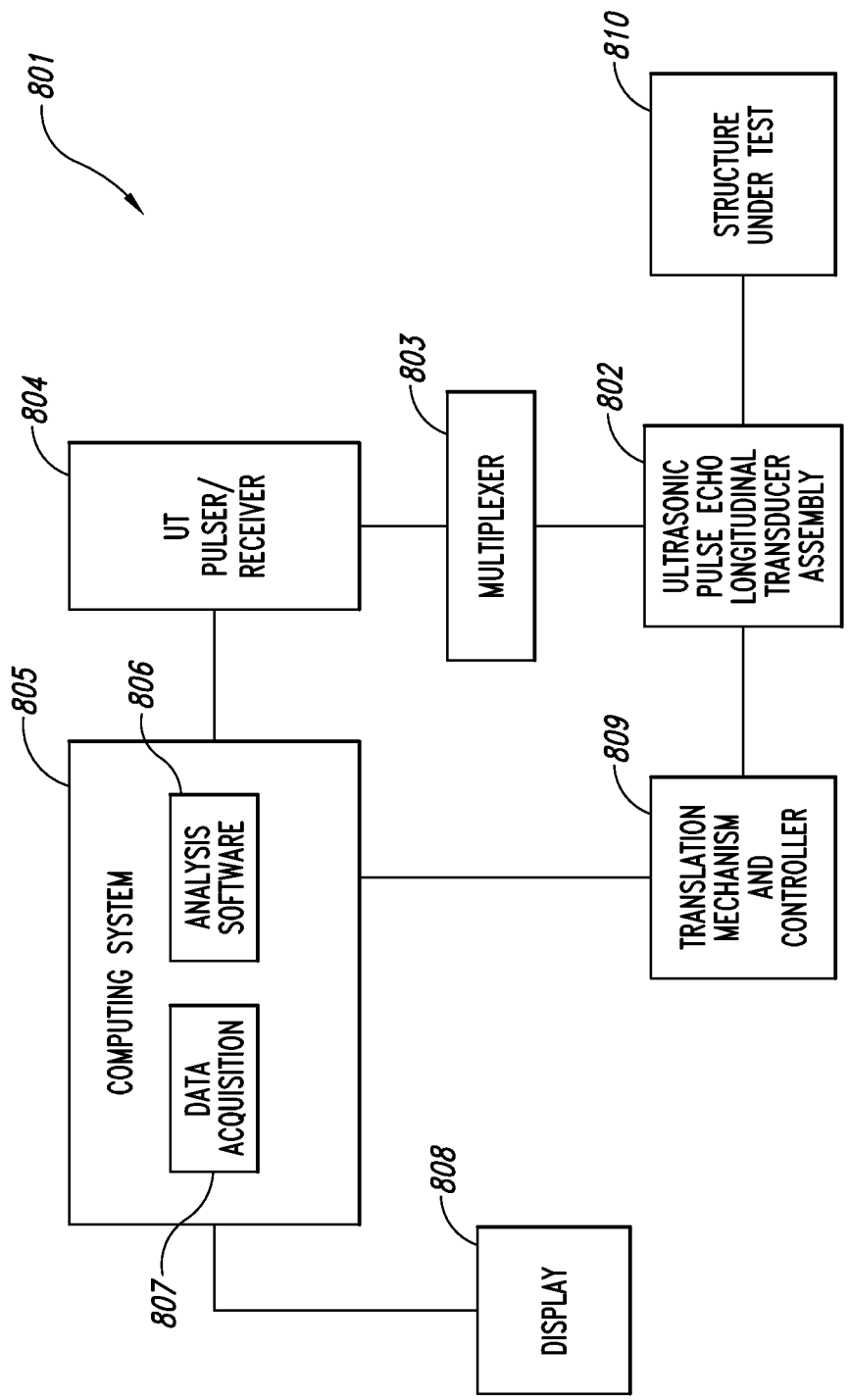
FIG. 8 is a block diagram of an ultrasonic inspection system disclosed herewith.

Another embodiment disclosed herein is the pulse echo ultrasonic inspection system 801 illustrated in FIG. 8. The non-limiting, exemplary system includes at least one ultrasonic transducer assembly 802, and when positioned proximate to the open edge of a hole or cutout within a structure 810, can be used to determine the condition of the structure. At least one ultrasonic pulser/receiver 804 is operatively coupled to the at least one ultrasonic transducer assembly 802. A computing system 805 is operatively coupled to the ultrasonic pulser/receiver. The computing system includes a data acquisition component 807 configured to acquire data from the ultrasonic pulser and receiver and a data analysis component 806 configured to analyze the acquired data. The data analysis component may be further configured to analyze the acquired data for the condition of the structure, including an anomaly such as a delamination, crack and or disbonding, and to display results on a display unit 808. The system is optionally configured to utilize multiple transducers with a multiplexer 803. The system may also be configured to include a translation mechanism and controller 809 for moving the transducer up and down into a hole, as well as circumferentially in a hole and be moved to other holes. During inspection, the data acquisition component 807 coupled to the ultrasonic pulser/receiver 804 shows the signals on the display 808, for example the corners of the reflective element, and the wave launched from the exit point of the transducer rod into the entry point of the structure.

Those skilled in the art will recognize that often elements making up a system can be rearranged, and not all elements need to be used at once, as is the case with this disclosure. For example, a multiplexer 803 may be used for controlling multiple ultrasonic longitudinal wave transducer assemblies 802, but it may not be necessary for controlling a single ultrasonic transducer assembly. Similarly, one might not use the display 808, or a translation mechanism 809, and not all portions may be hard wired, being wireless instead. In other words, one or more of the disclosed elements may be rearranged or removed from the disclosed system configuration, and the scope of the invention will remain. Further, the system is not limited by the elements disclosed, since there are numerous accessories that may be added without altering the general scope of the invention.

Figure 9A:
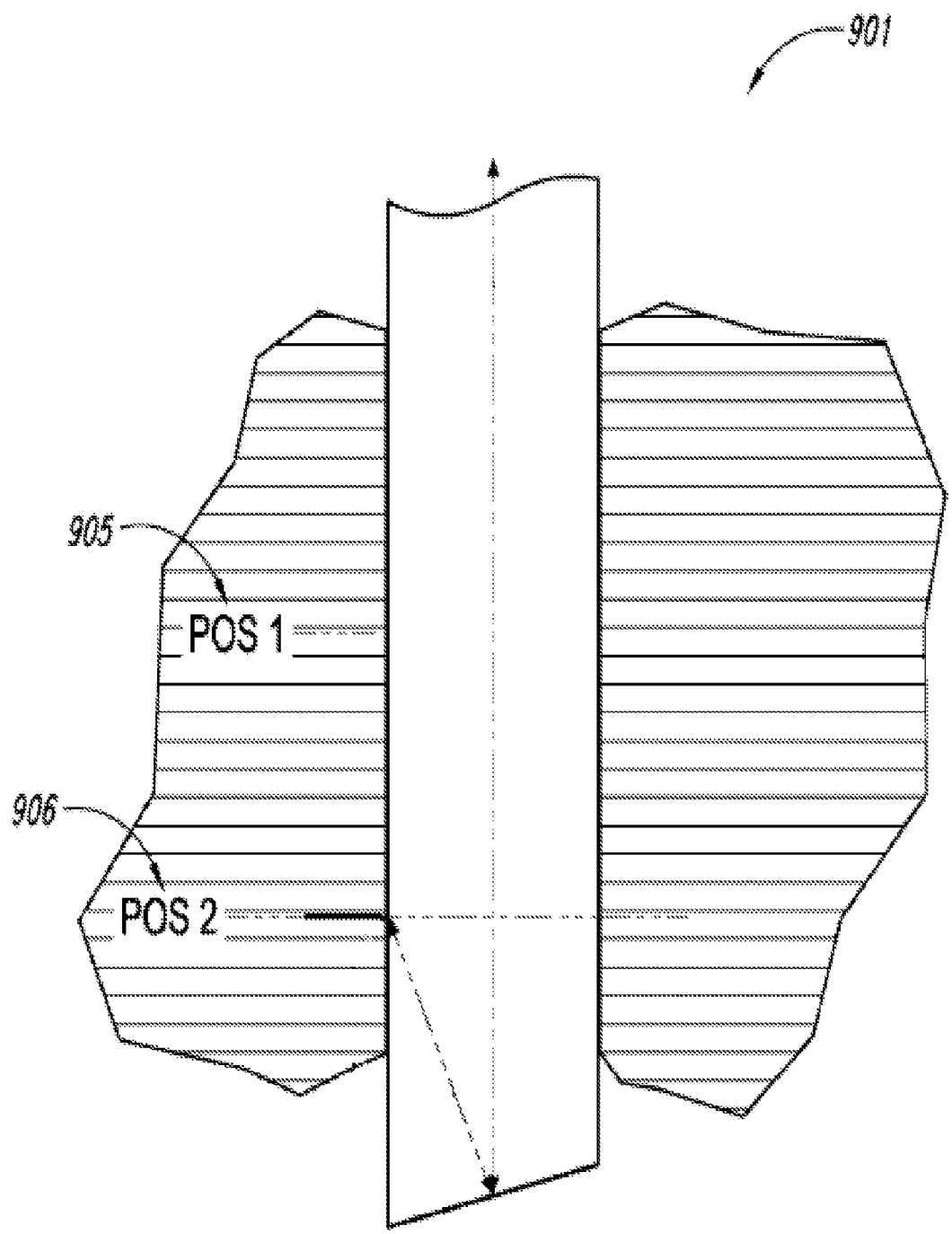
FIGS. 9A, 9B, and 9C are an illustration of signal data received from the inspection system as the longitudinal transducer is positioned at two different areas along an edge. Position 1 depicts a nominal area, and position 2 depicts an area with a delamination.
Figure 9B:
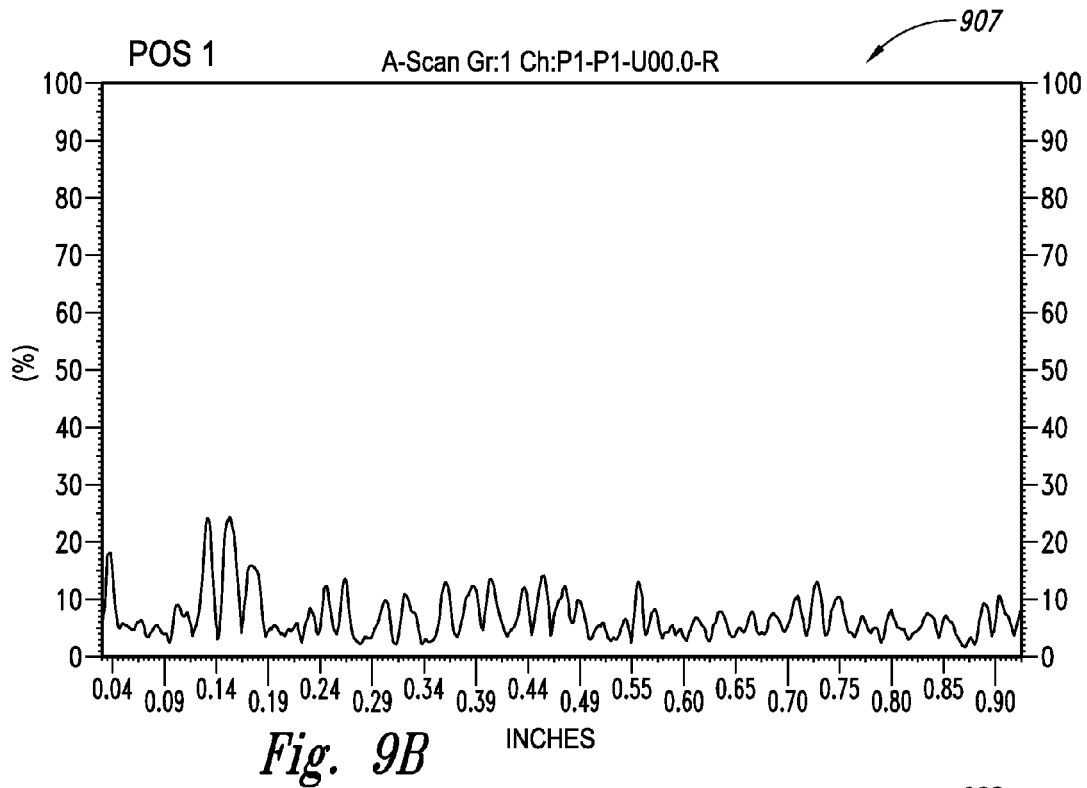
Figure 9C:
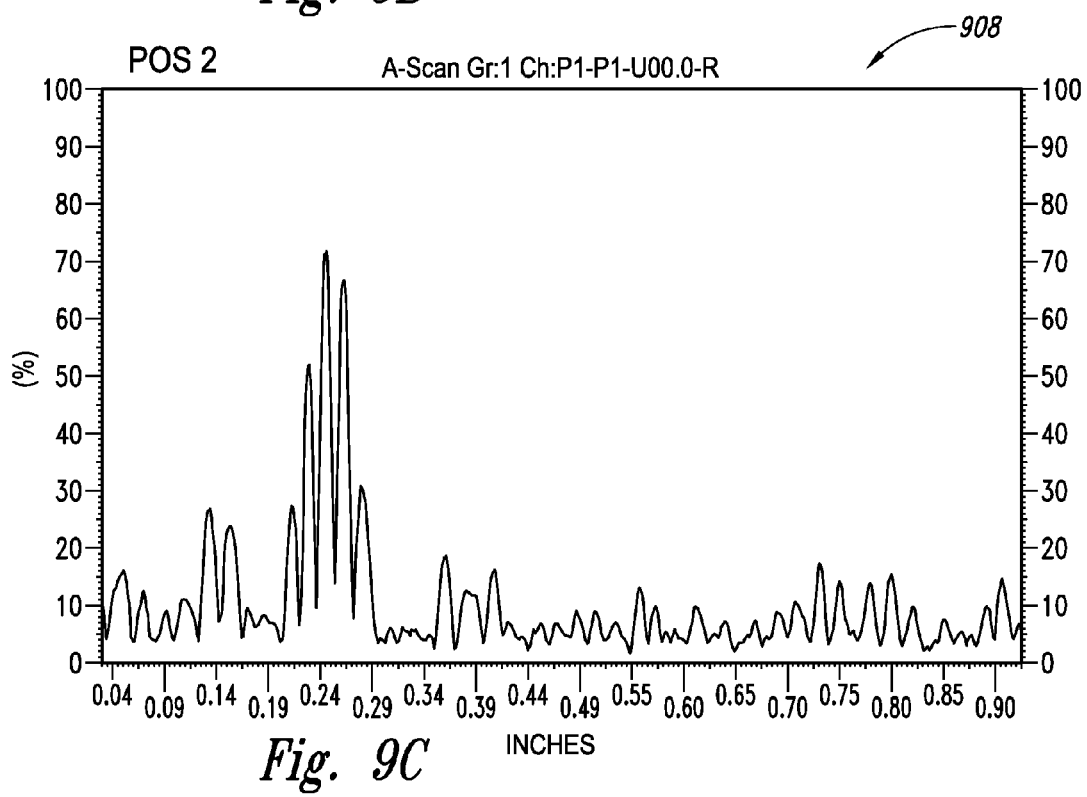

FIG. 9A illustrates a transducer rod 901 as it is moved up and down or rotated circumferentially in a hole or cut out in the structure. In this example, as the longitudinal wave is launched into two different ply depths (Position 1 and Position 2) of the structure, the returning echo results are displayed. FIG. 9B illustrates the displayed test results 907 for Position 1 (905) in the hole location that is an area with no flaws. FIG. 9C shows the displayed test results 908 at Position 2 (906) and exhibiting a delamination.

A fourth embodiment disclosed is a method of nondestructive inspection (NDI) of an airplane utilizing the disclosed apparatus and similar methods. The disclosed apparatus and method may be utilized to determine the condition of an airplane, for example, if a delamination discovered in an airplane wing skin also exists in the bonded airplane wing stiffener. NDI is a general term used for a variety of methods for evaluating structures, and can be required to be conducted by certified personnel in accordance with written procedures as defined in the enterprise non-destructive test specifications, and used for acceptance of parts, structures or components on airplanes or other vehicles. The ultrasonic transducer assembly can be advanced incrementally into the drilled hole and scanned circumferentially. Any signals occurring would be noted as depth in the hole and as circumferential position. The device is then incremented further and the process repeated to obtain a map of all damage open to the hole. The process may also be automated to produce a C-scan.

Figure 10:
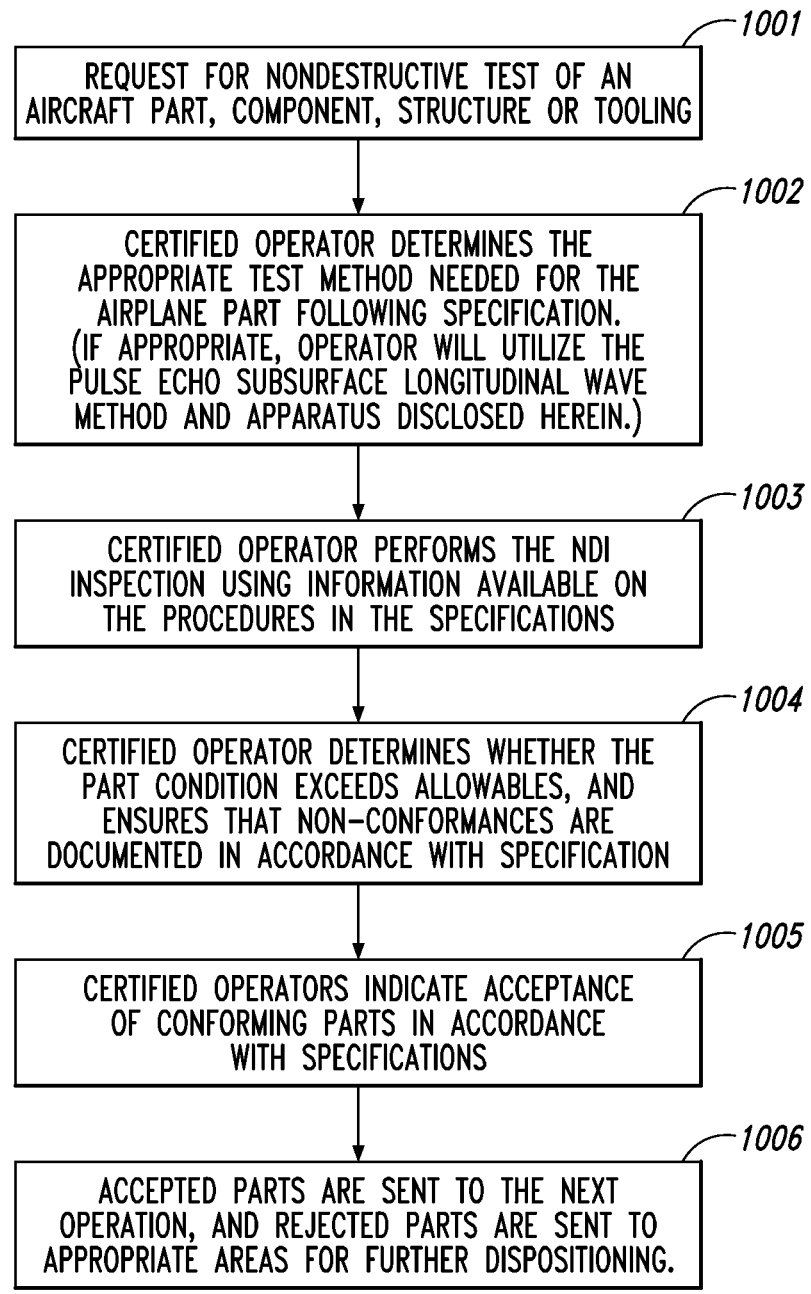
FIG. 10 is a flowchart illustrating one variation of the method for inspecting an aircraft part, structure or tooling.

One variation of this method is illustrated in FIG. 10. Upon receiving a request (1001), the operator selects the disclosed pulse echo longitudinal wave ultrasonic wave inspection method as the appropriate NDI test method needed for a particular airplane part following a specification 1002, and performs the inspection using the disclosed system and information available on the procedures in the specifications 1003. The operator determines whether the part condition exceeds allowables 1004, and ensures that non-conformances are documented in accordance with specifications. Certified operators indicate acceptance of conforming parts in accordance with specifications 1005. Accepted parts are sent to the next operation, and rejected parts are sent to appropriate areas for further dispositioning 1006.

Additional features of the disclosed apparatus described herein after form the subject of the claims of the disclosed apparatus. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims. This application is intended to cover any adaptations or variations of the present invention. The following claims are in no way intended to limit the scope of the invention to the specific embodiments described herein.

What is claimed is:

1. An ultrasonic transducer assembly comprising:
 a transducer;
 a transducer rod having a first end, a second end, and a propagation axis;
 the transducer is mechanically coupled to the first end of the transducer rod;
 the second end of the transducer rod includes a reflective rod element having at least a portion oriented non-normal to the propagation axis of the transducer rod;
 the transducer configured to transmit an ultrasonic sound wave that propagates along the propagation axis through the transducer rod and reflects off the reflective rod element at a first angle toward a side of the transducer rod;
 wherein the first angle is determined based on a material composition of the transducer rod so that the ultrasonic sound wave refracts when reaching an exit point on the side of the transducer rod and is launched at a second angle that is substantially parallel to a surface of the side of the transducer rod.

2. The ultrasonic transducer assembly of claim 1, wherein:
 the reflective rod element comprises a single flat face angled toward the side of the transducer rod.

3. The ultrasonic transducer assembly of claim 2, wherein:
 the first angle is approximately 40-85 degrees from the propagation axis.

4. The ultrasonic transducer assembly of claim 1, wherein:
 the reflective rod element comprises a curved face.

5. The ultrasonic transducer assembly of claim 1, wherein:
the reflective rod element comprises a conical face.

6. The ultrasonic transducer assembly of claim 1, further comprising:
a translating mechanism configured to move the transducer rod vertically or circumferentially inside a hole of a laminated structure.

7. The ultrasonic transducer assembly of claim 1, further comprising:
a second transducer embedded in the transducer rod between the first end and the second end;
the second transducer configured to transmit a second ultrasonic sound wave directly toward the side of the transducer rod without a reflection off the reflective rod element.

8. An ultrasonic transducer assembly comprising:
a transducer;
a transducer rod having a first end, a second end, and a propagation axis;
the transducer is mechanically coupled to the first end of the transducer rod;
the second end of the transducer rod includes a reflective rod element having at least a portion oriented non-normal to the propagation axis of the transducer rod;
the transducer configured to transmit an ultrasonic sound wave that propagates along the propagation axis through the transducer rod and reflects off the reflective rod element at an angle toward a side of the transducer rod;
wherein the reflective rod element comprises multiple faces.

9. A system for inspecting a laminated structure, the system comprising:
test instrumentation; and
a transducer assembly including a transducer rod having a first end and a second end;
the first end of the transducer rod includes a transducer;
the second end of the transducer rod includes a reflective rod element;
the transducer is configured to transmit an ultrasonic sound wave that propagates along a propagation axis through the transducer rod and reflects off the reflective rod element at a first angle toward a side of the transducer rod, wherein the ultrasonic sound wave passes through the side of the transducer rod and is introduced at a second angle into a surface proximate to a hole or edge of the laminated structure to generate a subsurface longitudinal ultrasonic sound wave in the laminated structure that propagates substantially perpendicular to layers of the laminated structure;
the transducer is configured to receive at least one echo sound wave along a route of the ultrasonic sound wave, wherein the at least one echo sound wave indicates reflection of the subsurface longitudinal ultrasonic sound wave off an anomaly in a layer of the laminated structure;
the test instrumentation is configured to process the at least one echo sound wave to detect anomalies in the laminated structure.

10. The system of claim 9, wherein:
the first angle comprises an incident angle that produces a 90-degree refracted angle of the ultrasonic sound wave substantially perpendicular to the layers in the laminated structure to generate the subsurface longitudinal ultrasonic sound wave.

11. The system of claim 9, further comprising:
a translating mechanism configured to move the transducer rod vertically or circumferentially inside the hole or edge of the laminated structure.

12. The system of claim 9, wherein:
the test instrumentation is configured to convert the at least one echo sound wave into an electrical signal, and to analyze the electrical signal to differentiate the anomalies from nominal areas in the laminated structure.

13. The system of claim 9, wherein:
the laminated structure is associated with an aircraft.

14. The system of claim 9, wherein:
the transducer assembly further includes a second transducer embedded in the transducer rod between the first end and the second end;
the second transducer is configured to transmit a second ultrasonic sound wave directly toward the side of the transducer rod without a reflection off the reflective rod element.

15. The system of claim 9, wherein:
the reflective rod element comprises a single flat face angled toward the side of the transducer rod.

16. The system of claim 9, wherein:
the reflective rod element comprises a curved face.

17. The system of claim 9, wherein:
the reflective rod element comprises a conical face.

18. The system of claim 9, wherein:
the reflective rod element comprises multiple faces.

19. The system of claim 9, wherein:
the transducer comprises multiple transducer crystals.

* * * * *